United States Patent [19]

Ruiz

[11] Patent Number: 4,790,311
[45] Date of Patent: Dec. 13, 1988

[54] RADIO FREQUENCY ANGIOPLASTY CATHETER SYSTEM

[76] Inventor: Oscar F. Ruiz, 3655 Bay Homes Dr., Coconut Grove, Fla. 33133

[21] Appl. No.: 5,120

[22] Filed: Jan. 20, 1987

Related U.S. Application Data

[63] Continuation-in-part of Ser. No. 870,152, Jun. 3, 1986, abandoned.

[51] Int. Cl.$^4$ .............................. A61B 17/38
[52] U.S. Cl. .................................. 128/303.1
[58] Field of Search ............ 128/303.1, 395–398, 128/804, 303.14

[56] References Cited

U.S. PATENT DOCUMENTS

| | | | |
|---|---|---|---|
| 4,154,246 | 5/1979 | LeVeen | 128/804 |
| 4,674,481 | 6/1987 | Boddie, Jr. | 128/804 |
| 4,682,596 | 7/1987 | Bales, et al. | 128/303.14 |

FOREIGN PATENT DOCUMENTS

| | | | |
|---|---|---|---|
| 2826383 | 12/1979 | Fed. Rep. of Germany | 128/303.1 |
| 8404879 | 12/1984 | World Int. Prop. O. | 128/303.1 |

Primary Examiner—Lee S. Cohen
Attorney, Agent, or Firm—Polster, Polster & Lucchesi

[57] ABSTRACT

Plaque removal system with a catheter having a long, generally flexible portion of a first material, an intermediate portion of a second thermally insulating material and a heatable tip portion of a third material. The tip is grounded and focuses radio frequency waves upon the tip to heat the tip. The position of the tip is determined by dispensing a contrast medium out the distal end of the catheter and viewing the vessel and catheter by x-ray. The heated tip is pushed forward through the vessel blockage to vaporize or otherwise disintegrate the plaque, which clears a path through the vessel.

13 Claims, 2 Drawing Sheets

RADIO FREQUENCY ANGIOPLASTY CATHETER SYSTEM

REFERENCE TO PRIOR APPLICATION

This is a continuation-in-part of application Ser. No. 870,152 filed June 3, 1986, now abandoned.

BACKGROUND OF THE INVENTION

The present invention relates to medical devices for removing and/or breaking down occlusions or other blockages in blood vessels and more particularly to a catheter employing a heatable tip for removing and/or breaking down such occlusions or blockages so as to restore the normal flow of blood within the cardiovascular system.

Atherosclerosis is a major cause of heart disease in the United States. In atherosclerosis a plaque forms which, if allowed to accumulate, can occlude the artery completely. In the past, angiographic catheters have been used to clear a blocked vessel by, for example, scraping a vascular wall by using a needle attached to the distal end of a catheter, as in U.S. Pat. No. 4,465,072 to Taheri.

Balloons connected to catheters have been used in a procedure called angioplasty to compress the plaque to open the vessel. A similar approach is shown in U.S. Pat. No. 4,589,412 to Kensey in which a cutting tip at the distal end of a catheter is rotated by the application of fluid pressure to cut away the plaque on the vessel walls. This catheter also includes a balloon which is disposed proximal of the cutting tip and is inflatable to protect against possible perforation of the artery. Two significant drawbacks of the these types of devices reside in the danger of passing a sharp object, such as a scraping needle or cutting tip, through a blood vessel, and, repeated inflation and deflation of a balloon in the blood vessel results in a residual state of stress and/or fatigue being imposed upon the walls of the vessel.

It is well known that fatiguing or otherwise traumatizing the walls of a blood vessel has an adverse effect on the bioelectrical properties of said vessel. Such an effect can have drastic long term consequences when it is realized that blood in its normal pH is negatively charged, and that there is approximately a one to five millivolt potential difference across the wall of a blood vessel. Should that potential difference decrease for any reason, such as where the vessel is traumatized and thrombosis is induced, blockage may build up on the vessel wall. For instance, as reported by Schwartz in a 1959 article "Prevention and Production of Thrombosis by Alterations in Electric Environment", Surgery, Gynecology and Obstetrics, page 533, and page 536, May 1959, the imposition of five millivolts of positive potential upon a segment of superficial femoral vein which has been occluded proximally results in thrombosis after one hour.

Laser beam angioplasty is becoming well established as having significant potential in the treatment of totally or severely obstructed blood vessels. In laser beam angioplasty a laser probe is first used to vaporize a minute pathway through the plaque. A small guide wire is slid through that pathway and a balloon catheter is passed over the guide wire to dilate the vessel in the conventional manner. U.S Pat. No. 4,207,874 to Choy describes such a laser tunnelling device which includes a fiber optic bundle for actually viewing the occlusion, a laser for vaporizing a tunnel through the occlusion, an injection port for radiopaque material so that the tip of the catheter may be accurately located, and a suction port for removing the vaporized material. Other such laser angioplasty devices are known. See for example, U.S. Pat. No. 4,627,436 to Leckrone.

Laser beam angioplasty systems are not without disadvantages. For one, the laser beam creates a very small pathway through the plaque. Moreover, these systems are not equally effective against all types of blockages due to the color absorptive specificity of various components of the atheroma and thrombi. In addition, there exists the possibility of perforation of the vessel by a laser beam focused too long on the vessel wall or positioned at an angle too acutely with respect to the vessel wall. Also many laser beam angioplasty systems lack the capability of being used with a guidewire to guide the laser catheter accurately to the occlusion.

According to the Sept. 3, 1986 issue of the *Medical Tribune,* Trimedyne, Inc. of Santa Ana, Calif. has a laser probe for coronary angioplasty having a metal alloy tip at the end of the probe which is heated by a laser beam to 400° C. to vaporize obstructions in blood vessels. Apparently this probe is led to the obstruction over a guide wire placed in the blood vessel.

Radio frequency energy has previously been used in medical surgery. Such devices both cut and cauterize as illustrated by U.S. Pat. No. 3,089,496 to Degelman, for example. However, it is believed that such devices in the past have been ill-suited for the vaporization and removal of plaque in blood vessels because of the possibility of perforation of the vessel wall, and because of the size and complexity of such devices.

SUMMARY OF THE INVENTION

It is accordingly an object of the present invention to provide a catheter which utilizes a heatable tip for opening a passage through plaque or debris so as to restore the normal flow of blood within the cardiovascular system.

Another object of this invention to provide a simple low cost system for eliminating or reducing blockage in a blood vessel.

It is yet another object of this invention to provide a catheter that has a tip heatable by radio frequency waves and that may be moved through the vessel blockage to vaporize the blockage.

It is a further object of the invention to provide a dye exit and/or entrance in the heatable tip of a catheter to facilitate the proper placement of the catheter and/or to flush the vessel.

Other objects and features of the present invention will be in part apparent and in part pointed out hereinafter.

In general, the catheter of the present invention comprises an elongated, cylindrical flexible hollow body member sized and shaped for insertion into a blood vessel. Extending throughout the interior of said body member is a dye conduit which provides a flow passage for radiopaque dye. The dye conduit may be the main lumen of the catheter or an auxiliary lumen as desired. The main lumen also provides a space for a grounding wire, although alternatively the grounding wire may have its own lumen or be embedded in the wall of the catheter.

Adjacent the distal end of the flexible body member is a short hollow length of thermally insulative and electrically non-conductive material sealingly secured between the catheter flexible body member and a heatable tip. The tip is a highly conductive material such as tungsten, titanium or other material suitable for being energized by radio frequency waves to produce heat. The heated tip at a suitable temperature of 350° C. or so is used to vaporize or otherwise disintegrate plaque or other deposits in the vessel upon contact. The catheter itself is capable of withstanding much higher temperatures of 700° C. or more. Operation at these higher temperatures, or at lower temperatures such as 100° C. suitable for melting fat, are within the scope of the present invention. The tip forms the distalmost end of said catheter. The tip is bullet-shaped and has an opening near its distalmost point. The distal end of the dye conduit is sealingly connected in fluid communication to said opening for allowing the discharge of radiopaque dye or other contrast media under pressure into the vessel.

The grounding wire is electrically connected to the heatable tip to cause radio frequency waves to focus on the tip and thereby heat the tip. The grounding wire may be disposed axially within the catheter body and has one end connected to the inside of the tip. The other end of the grounding wire is grounded outside of the vessel. The heat of the tip is controlled by the frequency or amplitude of the output of a radio frequency generator.

BRIEF DESCRIPTION OF THE DRAWINGS

Similar reference characters indicate similar parts throughout the several views of the drawings.

DESCRIPTION OF THE PREFERRED EMBODIMENT

Figure 1:
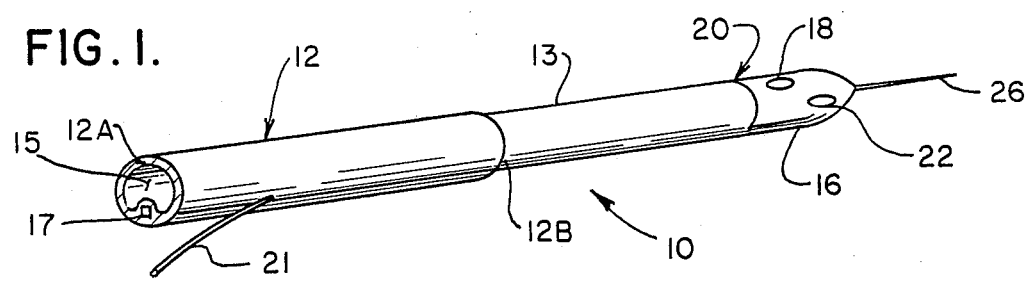
FIG. 1 is a perspective view of a catheter of the present invention.

Referring now to the drawings, FIG. 1 shows a catheter 10 of the present invention including an elongated cylindrical flexible hollow body member 12 of suitable thermoplastic material having an entrance end 12A and an exit end 12B. Flexible member 12 is generally sized and shaped for an insertion into a blood vessel. For example, and not by way of limitation, it has the same outer diameter as a 5 Fr. (0.066") catheter. Body 12 has a main opening or lumen 15 extending the length of body member 12. Extending generally axially through the interior of catheter 12 is a secondary conduit or lumen 17 for providing a flow passage for fluids such as radiopaque dye. Of course, radiopaque dye or other contrast media could be supplied through main conduit 15 in those cases where a greater flow rate is desired. Although the secondary conduit 17 is shown having a diameter less than the inside diameter of opening 15, the relative sizes of the two conduits is determined by the desired flow rates through the respective conduits. The proximal end of conduit 17 preferably exits body member 12 through the side wall thereof as shown in FIG. 5, but alternatively it may terminate at the same point as proximal opening 15 of body member 12.

Distal end 12B of body member 12 is secured to a short hollow insulator 13 of thermally insulative and electrically non-conductive material such as a ceramic. Insulator 13 has one end sealingly connected to a tip portion 16 by adhesives or mechanical bonding and the other end is suitably secured to body member 12.

Figure 4:
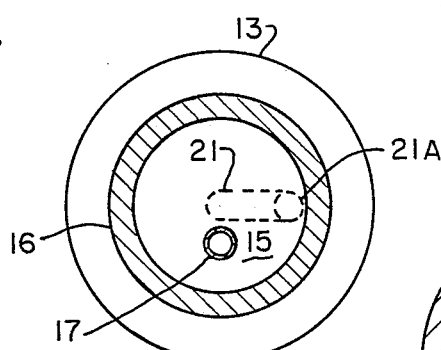
FIG. 4 is a cross sectional view taken along lines 4—4 in FIG. 5.

Tip portion 16 is fabricated preferably of a highly conductive material such as tungsten or titanium or any other material such as stainless steel that will respond to radio frequency waves transmitted to tip 16 without failing structurally due to the high temperatures generated. A grounding wire 21 connected to an external ground passes through portions 12 and 13 and into tip 16. Grounding wire is suitably secured to the inside of tip 16 as indicated at 21A (FIG. 4) to ground the tip. Once grounded the tip acts as an antenna to focus incident radio frequency waves upon the tip. As a result the tip is heated to temperatures in the vicinity of 350° C. or so. The catheter itself is capable of withstanding tip temperatures of 700° C. or higher without failing. It should be appreciated that a temperature of 100° C. is sufficient to melt fatty deposits in the blood vessels while temperatures of 350° C. or 400° C. and higher as generated by the present apparatus instantly vaporize fatty deposits and plaque without significant charring of the surrounding tissue. As used herein the term "disintegrate" is used to cover melting, burning and/or breaking down of such deposits. Tip portion 16 forms the distalmost end of said entire catheter 10 and is shaped similar to a bullet. The tip has openings 18, 22 and 23 (FIG. 2) therein.

Figure 5:
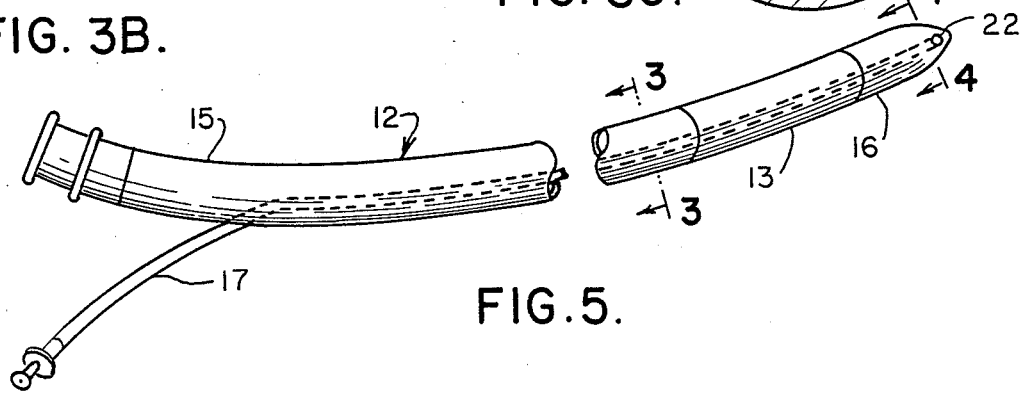
FIG. 5 is a side view of the catheter with a main conduit fluid connector and a second conduit fluid connector.

The proximal end of insulator 13 is sealingly connected to catheter body member 12, forming a complete or entire catheter 10 beginning at the proximal end in FIGS. 1 and 5 and ending at tip portion 16. The distal end of dye conduit 17 is sealingly connected in fluid communication with opening 22 of tip portion 16, facilitating the discharge of radiopaque dye or other fluids into the occupied blood vessel for determining with the aid of x-ray photography the position of the catheter tip portion and of the occlusion sought to be opened. The conduits 15 and 17 and exits 18 and 22 in fluid communication respectively therewith may be used to flush the vessel 80 (FIG. 6) between the tip means 16 and occlusion 90.

Figure 2:
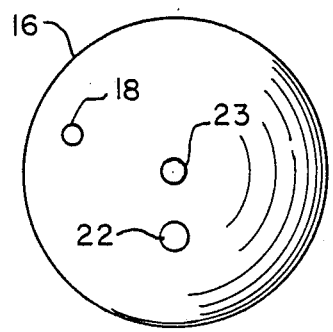
FIG. 2 is a distal end view of the heatable tip on the right side of the catheter shown in FIGS. 1 and 5.

As shown in FIG. 2, openings 18 and 22 are displaced from the axis of tip 16 while opening 23 lies on the axis. The exact placement of openings 18 and 22 may be varied and, if sufficient flow rates can be achieved, these openings may even be in the plastic body portion 12 of the catheter instead of in tip 16. Opening 23 lies on the axis of tip 16 so that a small thin guide wire 26 (FIG. 1) may be inserted therethrough for the purpose of facilitating the maneuvering of catheter 10 to the point of treatment.

Figure 3A:
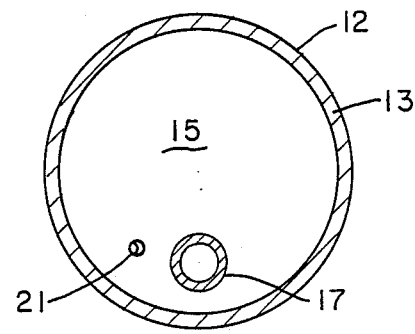
FIG. 3A is a cross sectional view taken along lines 3—3 in FIG. 5.
Figure 3B:
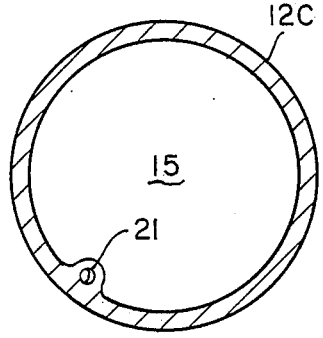
FIG. 3B is a view similar to FIG. 3A showing an alternative construction of the catheter of the present invention.
Figure 3C:
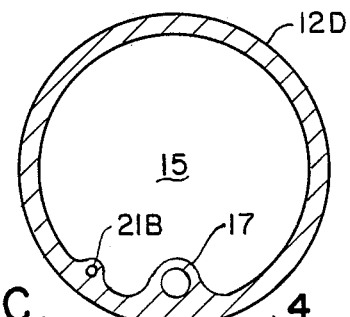
FIG. 3C is a view similar to FIGS. 3A and 3B showing another alternative construction of the catheter of the present invention.

FIG. 3A illustrates one embodiment of the present invention in which grounding wire 21 passes through main lumen 15 and conduit 17 forms a separate lumen in the catheter. An alternative construction is shown in FIG. 3B in which the grounding wire 21 is embedded in the wall of a body member 12C and only a single lumen 15 is present. In this second embodiment injection of the contrast medium is accomplished through the main lumen. A third construction is shown in FIG. 3C. In this construction lumen 17 is shown attached to the wall of body member 12D and a third lumen 21B is provided for the grounding wire. Of course lumen 17 could be used for inflating a balloon on the catheter in the well-known balloon angioplasty procedure if lumen 17 were suitably connected to the interior of a balloon (not shown) disposed on the catheter. In this case, the injection of contrast media could not occur through lumen 17. It should be appreciated that these constructions are merely illustrative and various combinations thereof could be made without falling outside the scope of the present invention. Catheters with greater numbers of lumens or with lumens of different or various sizes are also with the scope of the present invention.

Figure 7:
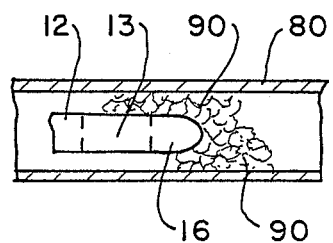
FIG. 7 illustrates the catheter tip passing through blockage in the blood vessel.
Figure 8:
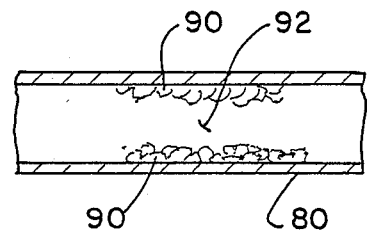
FIG. 8 illustrates the blockage in the blood vessel after the tip has passed through the blockage.

In summary, the entire catheter 10 of FIGS. 1 and 5 includes body member 12 of a first material, such as plastic, connected to an intermediate insulating portion 13 made of a second material such as a ceramic, to insulate the catheter from heat and/or electrical charging, and a tip portion 16 of a third highly conductive material such as tungsten or titanium, or any other well known material which heats up rapidly and retains its shape, at the distal end of the entire catheter 10. Once heated to its operating temperature, catheter 10 as shown in FIG. 5 is pushed through the blockage 90 as shown in FIG. 7 to vaporize or otherwise disintegrate the blockage to provide a clear path 92 in the vessel as shown in FIG. 8.

Figure 6:
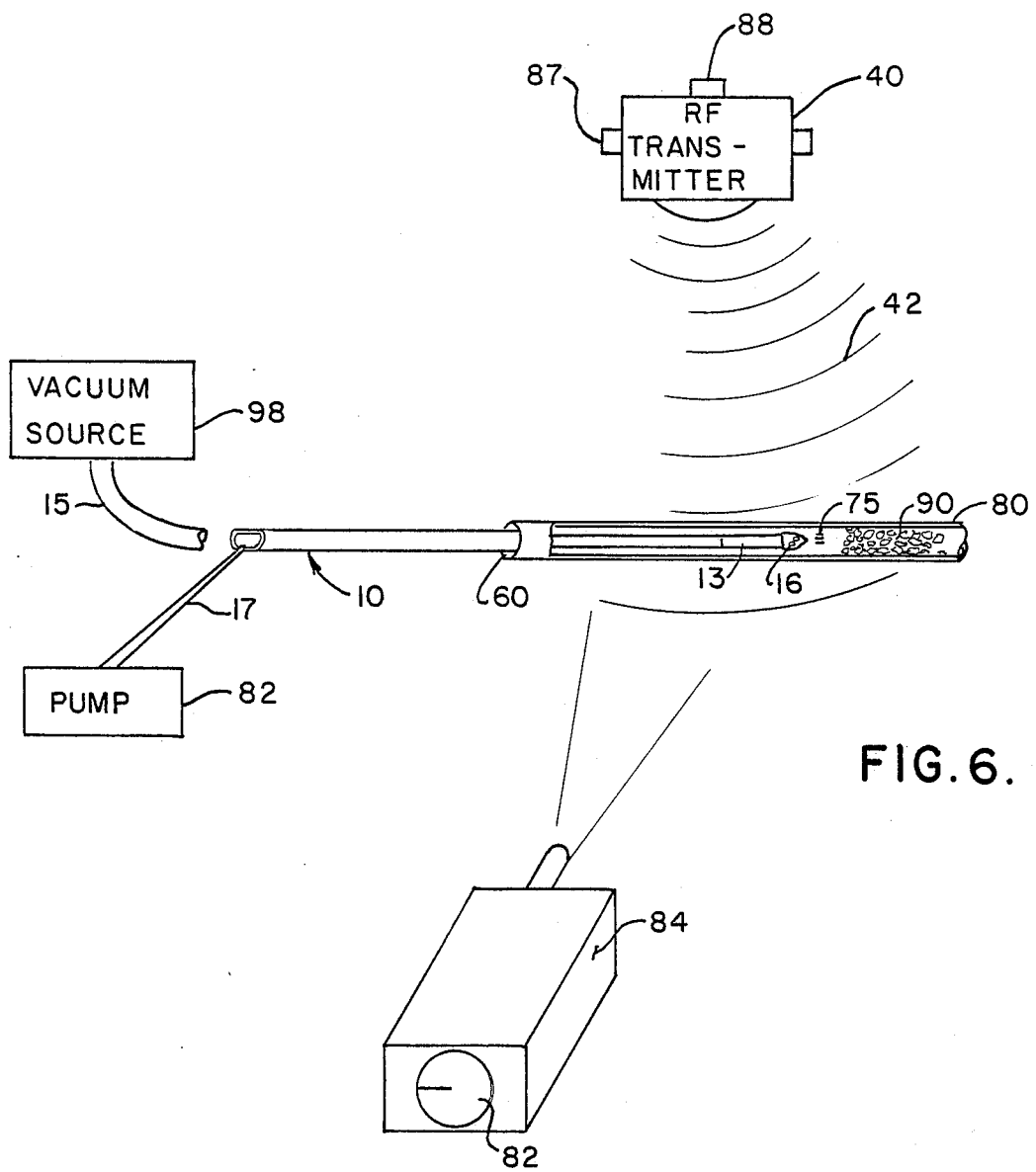
FIG. 6 is an illustration of the system of the present invention with the catheter tip adjacent blockage in a blood vessel.

In use, catheter 10 is inserted into a blood vessel 80 (FIG. 6) at the location labelled 60 using any well known procedure. The catheter is pushed into the blood vessel to the vicinity of an occlusion 90. Radiopaque dye 75 is discharged, using a pump 82 connected to dye conduit 17, through opening 22 into the surrounding cardiovascular region of the body. Of course, in the case of an occlusion in a coronary artery, the injection of dye would be made manually. Using ordinary x-ray means 84, the positions of the catheter tip 16 and of any occlusion 90 are locatable by viewing the scope or cathode ray tube 82. Alternatively, the catheter may be disposed in a guiding catheter and/or over a guidewire which has already been positioned in the vicinity of the occlusion. Upon positioning the catheter tip 16 at the point of treatment as shown in FIG. 6, a radio frequency wave transmitter 40 for transmitting radio waves 42 is activated. Waves 42 are directed toward tip portion means 16 for energizing the same. Since tip 16 is grounded, it acts to focus the energy on the tip itself, causing tip portion means 16 to undergo a rapid temperature increase to the vicinity of 350° C. or higher. As explained below, the actual temperature may be modulated by the user as desired for a particular application. Insulating section 13 protects body portion 12 from these extreme temperatures. The tip is then pushed through the blockage 90 as shown in FIG. 7 to vaporize the plaque or other debris to clear a path 92 as shown in FIG. 8. Tip portion 16 may be selectively or periodically energized to keep said tip below a predetermined temperature to avoid damaging the vascular walls.

More specifically, the temperature of the tip may be controlled by varying the frequency of the radio frequency generator by use of a frequency control means 87 or by varying the amplitude of the radio frequency waves by adjusting an amplitude control means 88.

The blood vessel may be flushed during the above procedure by dispensing a salt solution out exit 22 and taking the dispensed solution and vaporized occlusion particles out of the blood vessel by a vacuum source 98 through opening 18 and channel 15. Of course, in the case of a single lumen catheter, dispensing of the salt solution and the application of suction would occur sequentially using the same lumen. Flushing and suction may be provided to extract the dissolved or broken up debris from the vessel or for cooling the tip member with the flushing fluid.

It should also be noted that the instant invention may be used jointly with a balloon for compacting the plaque in the blood vessel in a well known procedure. The balloon means would be inserted after the path is cleared as shown in FIG. 8, or the catheter 10 could include a balloon section.

The instant invention has been shown and described herein in what is considered to be the most practical and preferred embodiment. It is recognized, however, that departures may be made therefrom within the scope of the invention and that various modifications will occur to a person skilled in the art.

What I claim is:

1. A method for unblocking fluid channels such as blood vessels in the body of an animal which are blocked or partially blocked by natural debris such as plaque, comprising the steps of:
   inserting a catheter into the vessel, said catheter having a heatable, groundable tip, a flexible conduit proximal portion, and means extending through the flexible conduit proximal portion for grounding said tip, said means for grounding said tip being electrically connected to said tip;
   moving the catheter to the debris;
   grounding the heatable tip by connecting the means for grounding the tip to an external electrical ground;
   transmitting radio frequency waves from a source separate and removed from the catheter toward the body of the animal;
   heating the tip of the catheter by the self-focusing of electromagnetic waves thereon to provide a hot debris contact surface at a temperature of at least approximately 100° C., said heating step including the step of focusing the radio frequency waves, the grounded tip acting to focus the radio frequency waves to raise the temperature of the tip; and
   moving said heated tip of the catheter through the debris by disintegrating at least a portion of the debris by heat to open the vessel to natural flow.

2. A method for unblocking fluid channels such as blood vessels in the body of an animal which are blocked or partially blocked by natural debris such as plaque, comprising the steps of:
   inserting a catheter having distal and proximal ends in the vessel, said catheter having a hollow flexible conduit portion, and a heatable tip connected at the distal end of the catheter, said heatable tip providing a heatable external debris engaging surface;
   placing the catheter within the blocked vessel;
   positioning the catheter within the vessel utilizing detection apparatus;

transmitting radio frequency waves from a source separate and removed from the catheter in the direction of said positioned catheter;

focusing said radio frequency waves by the grounding of the heatable tip such that the catheter tip including the external, debris engaging surface is heated to an elevated temperature of at least approximately 100° C.;

applying the debris engaging surface to said debris, said heated catheter tip disintegrating said debris; and removing said disintegrated debris through the hollow, flexible conduit portion, whereby said method eliminates the blockage of said vessel.

3. The method for unblocking fluid vessels as set forth in claim 2, wherein the elevated temperature is at least approximately 350° C.

4. The method for unblocking vessels as set forth in claim 2 wherein the heatable tip is grounded by a grounding wire placed within the catheter.

5. The method for unblocking vessels as set forth in claim 2, further comprising a flexible dye conduit generally axially disposed within said flexible conduit portion, said dye conduit being fluidly connected to an exit in said heatable tip for ejection of dye into the vessel, said ejection of the dye being a portion of the positioning step.

6. The method for unblocking fluid vessels as set forth in claim 2, further including controlling the temperature of said heatable tip.

7. A catheter system for unblocking blood vessels of animals at least partially blocked by natural debris such as plaque, comprising;

a catheter with a proximal end and a distal end, said catheter having a flexible conduit portion and heatable tip means for receiving radio frequency waves while in the blood vessel to raise the heatable tip means to at least approximately 100° C. to disintegrate the debris, said heatable tip means being connected to the flexible conduit portion such that the conduit portion is shielded at least partially from the temperature of the heatable tip means so that the conduit portion retains its shape during operation;

a ground wire disposed in the catheter and electrically connected to the heatable tip means and adapted to be connected to an electrical ground external of the body of an animal into which the catheter is inserted; and means separate and removed from the catheter for transmitting radio frequency waves toward the body of the animal, the heatable tip means when grounded by the ground wire acting to focus the radio frequency waves to raise the temperature of the tip means.

8. The catheter system as set forth in claim 7 further including a dye conduit through the flexible conduit portion of the catheter for supplying a flow of radiopaque dye, and a dye opening in the heatable tip means in fluid communication with the dye conduit for injection of radiopaque dye in the vessel in the vicinity of the heatable tip means.

9. The catheter system as set forth in claim 7 wherein the flexible conduit portion includes at least one lumen for applying suction, said heatable tip means including an opening in fluid communication with the suction lumen to allow the suctioning of disintegrated debris from the vicinity of the heatable tip means, further including a suction source means for applying suction to the suction lumen.

10. The catheter system as set forth in claim 7 wherein the transmitting means includes control means for controlling the heating and duration of heating of the heatable tip means.

11. The catheter system as set forth in claim 7 including a thermal insulator section connected to the end of the flexible conduit portion closer to the distal end of the catheter and to the end of the heatable tip means closer to the proximal end of the catheter for thermally insulating the flexible conduit portion from the heatable tip means.

12. The catheter system as set forth in claim 11 wherein the material composing the heatable tip means and the material composing the thermal insulator section retain their shapes when the tip means temperature is greater than 400° C.

13. The catheter system as set forth in claim 12, wherein the materials of the heatable tip means and the thermal insulator section retain their shapes when the tip means temperature is in the general vicinity of 700° C.

* * * * *